United States Patent
Nguyen et al.

(10) Patent No.: US 6,530,399 B2
(45) Date of Patent: Mar. 11, 2003

(54) METHOD FOR DELIVERING LIQUID WITH A CONTAINER DELIVERY SYSTEM

(75) Inventors: Nick Ngoc Nguyen, Costa Mesa, CA (US); Ross G. Krogh, Rancho Santa Margarita, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/846,401

(22) Filed: May 1, 2001

(65) Prior Publication Data

US 2002/0157726 A1 Oct. 31, 2002

Related U.S. Application Data

(62) Division of application No. 09/499,418, filed on Feb. 7, 2000, now Pat. No. 6,279,622.

(51) Int. Cl.⁷ .................................................. B65B 3/04
(52) U.S. Cl. ............................... 141/2; 141/83; 141/94; 141/285; 141/319; 141/329; 141/330; 141/364; 141/366
(58) Field of Search ............................... 141/4, 5, 7, 8, 141/2, 59, 65, 83, 94, 311 R, 319–322, 329, 330, 285, 291, 363–366; 422/28, 298

(56) References Cited

U.S. PATENT DOCUMENTS

| | | |
|---|---|---|
| 4,642,165 A | 2/1987 | Bier |
| 4,731,222 A | 3/1988 | Kralovic et al. |
| 4,817,800 A | 4/1989 | Williams et al. |
| 4,869,286 A | 9/1989 | Williams et al. |
| 4,892,706 A | 1/1990 | Kralovic et al. |
| 4,899,519 A | 2/1990 | Williams et al. |
| 4,909,287 A | 3/1990 | Williams et al. |
| 4,909,999 A | 3/1990 | Cummings et al. |
| 4,913,196 A | 4/1990 | Williams et al. |
| 4,938,262 A | 7/1990 | Williams et al. |
| 4,941,518 A | 7/1990 | Williams et al. |
| 4,941,519 A | 7/1990 | Sestak et al. |
| 5,115,842 A * | 5/1992 | Crafts et al. ................. 141/113 |
| 5,122,344 A | 6/1992 | Schmoegner |
| 5,313,993 A * | 5/1994 | Corby et al. ................. 141/319 |
| 5,527,507 A | 6/1996 | Childers et al. |
| 5,656,238 A | 8/1997 | Spencer et al. |
| 5,887,716 A | 3/1999 | Williams et al. |
| 5,915,427 A * | 6/1999 | Grabenkort ................... 141/18 |
| 6,125,893 A * | 10/2000 | Braatz et al. ........... 128/200.21 |

* cited by examiner

Primary Examiner—Timothy L. Maust
(74) Attorney, Agent, or Firm—Knobbe, Martens, Olson & Bear, LLP

(57) ABSTRACT

A system and a method for delivering and metering a fixed volume of liquid, such as a liquid sterilant from a container into a vaporization system. The method for the delivering system includes the steps of sensing a requirement for additional liquid sterilant, determining whether the liquid sterilant to be added is acceptable for use, and delivering the liquid sterilant from a container into an accumulator. The method of metering the liquid sterilant into the vaporization system includes creating a vacuum in a chamber connected to the vaporizer and delivering the liquid sterilant into a vaporizer while continually sensing the flow of the delivery. The metering system maintains a slow, controlled flow in order to achieve efficient vaporization of the liquid sterilant and to provide accurate sensing of the gas/liquid interface.

29 Claims, 11 Drawing Sheets

| State | Description | Valve 1 | Valve 2 | Valve 3 | Valve 4 | Vacuum |
|---|---|---|---|---|---|---|
| 1 | Idle | Closed | Closed | Closed | Closed | Off |
| 2 | Evacuate Tube | Closed | Open | Closed | Closed | On |
| 3 | Fill Tube | Open | Closed | Closed | Closed | On |
| 4 | Inject | Closed | Open | Open | Closed | Off at Injection |
| 5 | Post Inject | Closed | Open | Closed | Closed | Off at Injection |
| 6 | Purge | Open | Closed | Closed | Open | On or Off |

FIG. 11

METHOD FOR DELIVERING LIQUID WITH A CONTAINER DELIVERY SYSTEM

RELATED APPLICATIONS

This application is a divisional of U.S. application Ser. No. 09/499,418, filed Feb. 7, 2000, now U.S. Pat. No. 6,279,622.

BACKGROUND OF THE INVENTION

1. Field of the Invention

The present invention relates to a system and a method of delivering and metering a liquid, and more particularly to a system and a method of delivering and metering a liquid sterilant from a container into a vaporization system. The vapor or gas produced by the vaporization system is typically used for sterilization and/or decontamination purposes.

2. Background of the Invention

In order to sterilize certain devices or apparatus, particularly in the medical field, the device or apparatus can be placed in a chamber where liquid sterilant is vaporized. In order to ensure effective and efficient sterilization, the liquid sterilant must be metered in accurately and reproducibly measured amounts into the vaporization chamber.

One conventional method of metering liquid sterilant into a vaporization chamber involves extracting predetermined doses of liquid sterilant from a sealed cell. A cassette holds a group of these cells and in order to extract a dosage from each cell, a dispensing apparatus punctures each cell individually and pneumatic pressure drives the liquid sterilant out of the punctured cell.

This method presents several problems. First, using cassettes of cells offers little flexibility because the amount of liquid sterilant drawn into the chamber is limited to the individual cell volume, or multiples thereof Secondly, in multi-phase or flow-through sterilization cycles where large volumes of liquid sterilant may be required, multiple cassettes are needed, making this method not only inflexible, but also uneconomical and impractical. Lastly, liquid sterilant (such as hydrogen peroxide) is susceptible to degrade into gases or vapors. When this degradation occurs, the gases or vapors may rupture the cassette cells unless the cells are vented. However, over time, venting reduces the concentration of the sterilant.

In another conventional method, the liquid sterilant is pumped from a reservoir into a vaporization chamber. The key to this method is the proper metering of the liquid sterilant in order to accomplish effective and efficient sterilization. Several control mechanisms exist to meter the proper amount of liquid sterilant, such as controlling the pump volume directly, controlling the revolution rate or dispensing time of a continuous flow, fixed output pump, and monitoring the weight loss of the reservoir as the liquid is pumped from the reservoir.

As with the conventional cassette method, these methods also suffer from difficulties associated with the degradation of the liquid sterilant over time. As discussed above, the liquid sterilant can degrade over time to form gases and vapors. Air bubbles created by the degraded gaseous sterilant will disrupt the effectiveness, efficiency, and accuracy of any of these control mechanisms. For example, air bubbles can cause a "vapor lock" in a stroke-type pump if it is allowed to remain idle for an extended period of time. Moreover, in a control mechanism which meters liquid sterilant by controlling the dispensing time period at a fixed pressure or vacuum, the liquid is pushed or sucked into the vaporizer, along with the air bubbles, in a non-uniform matter, causing significant decreases in efficiency and effectiveness. As a final example, the formation of gases and vapors will disrupt the effectiveness of a control mechanism which monitors weight loss from the liquid reservoir. When such a system remains idle for an extended period, the weight loss from the reservoir, as measured by the balance, will not account for the air bubbles formed in the dispensing lines, which are dispensed into the vaporizer at start-up.

In addition to the problems created when the liquid sterilant is allowed to degrade into gases and vapors over time, the conventional methods used to control the metering of the liquid sterilant face additional problems if they rely on high injection rates and high pressures. That is, in order to circumvent the problems of degradation described above, conventional control mechanisms apply high injection rates and high pressures in order to dispense the liquid sterilant as quickly as possible. However, these high injection rates and high pressures place an extra strain on the equipment and can often lead to system leaks. Moreover, due to the substances involved, compatibility problems may arise when attempting to reduce system leaks by constructing the equipment with certain types of material which can sustain such high pressures.

There is a need for a system and method of metering and delivering containers of liquid sterilant into a system which meters the liquid sterilant from a reservoir into a vaporization system. This process needs to be accomplished in accurately and reproducibly measured amounts. There is also a need for a metering system and method which can deliver a fixed and measured volume of the liquid sterilant into the vaporizer chamber at reduced flow rates to avoid system leaks and material compatibility problems. A flow sensor needs to be incorporated with such a system in order to achieve this objective.

SUMMARY OF THE INVENTION

According to the present invention, a system and a method is provided for delivering and metering a liquid, such as a liquid sterilant, from a container into a vaporization system.

In one embodiment of the invention, the delivering system comprises an accumulator for receiving a liquid from a container. The delivery system includes a sensor to determine a pre-defined specification of the accumulator, such as the level of liquid in the accumulator. The delivery system also includes a second sensor to determine a pre-defined specification of the container, such as whether or not the liquid in the container is acceptable for use. A delivery mechanism can be employed for loading the container into a carrier which can be opened by an operator after being released by a release mechanism. A second delivery mechanism can be employed for delivering the liquid in the container into the accumulator and a locking mechanism secures the container in this second delivery mechanism during the delivery of the liquid into the accumulator.

The method for this delivering system can include the steps of determining whether the liquid in the accumulator satisfies a pre-defined specification and then generating a signal prompting the loading of the container into the container delivery system. The delivering system can then determine whether the liquid in the container satisfies a second pre-defined specification and if so then release the container delivery system to accept the loading of the container into the container delivery system. Once the container is loaded into the container delivery system, the container is locked in order to secure the container in the container delivery system. When the container is locked in place, then the liquid is delivered from the container into the accumulator.

In one embodiment of the metering system, the invention can comprise an accumulator for delivering the liquid to a metering tube which delivers a metered volume of the liquid to the vaporizer. The metering system employs a plurality of valves which control the direction and flow of the fluid in the system. Moreover, the metering system includes a delivery mechanism for delivering the liquid from the accumulator to the metering tube at a first flow rate. A second delivery mechanism delivers the liquid from the metering tube to the vaporizer at a second flow rate, wherein the second flow rate is slower than the first flow rate.

The method for this metering system can include the steps of evacuating the vaporizer and the metering tube and then delivering the liquid from the accumulator into the metering tube at a first flow rate. Then the metering system can deliver the liquid from the metering tube into the vaporizer at a second flow rate, wherein the second flow rate is slower than the first flow rate. The metering system maintains a slow, controlled flow in order to achieve efficient vaporization of the liquid sterilant and to provide accurate sensing of the air/liquid interface.

BRIEF DESCRIPTION OF THE DRAWINGS

FIG. 11 is a table illustrating one embodiment of a method of a metering system.

DETAILED DESCRIPTION OF THE PREFERRED EMBODIMENT

Figure 1:
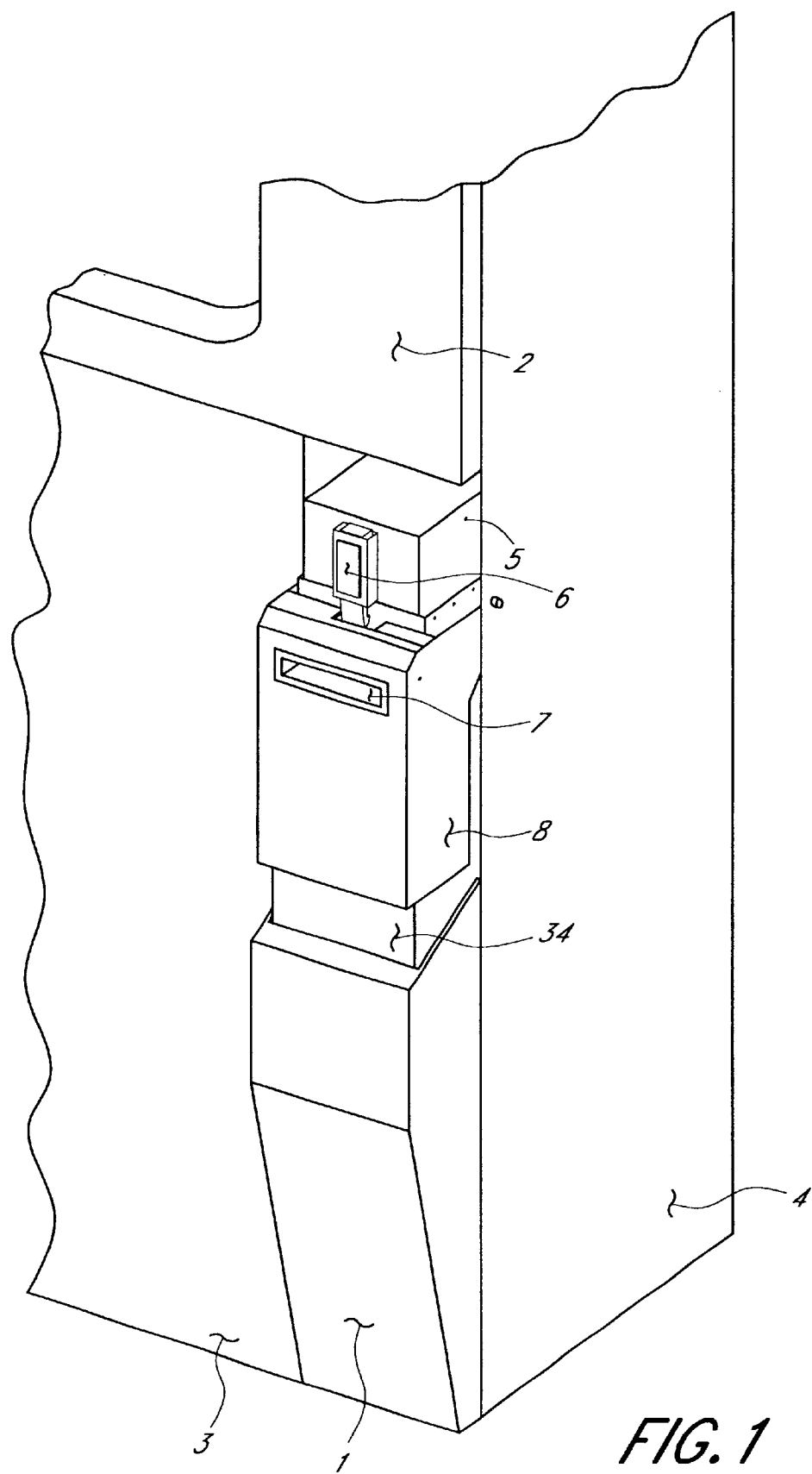
FIG. 1 is a perspective view of a container delivering system in the closed position.
Figure 2:
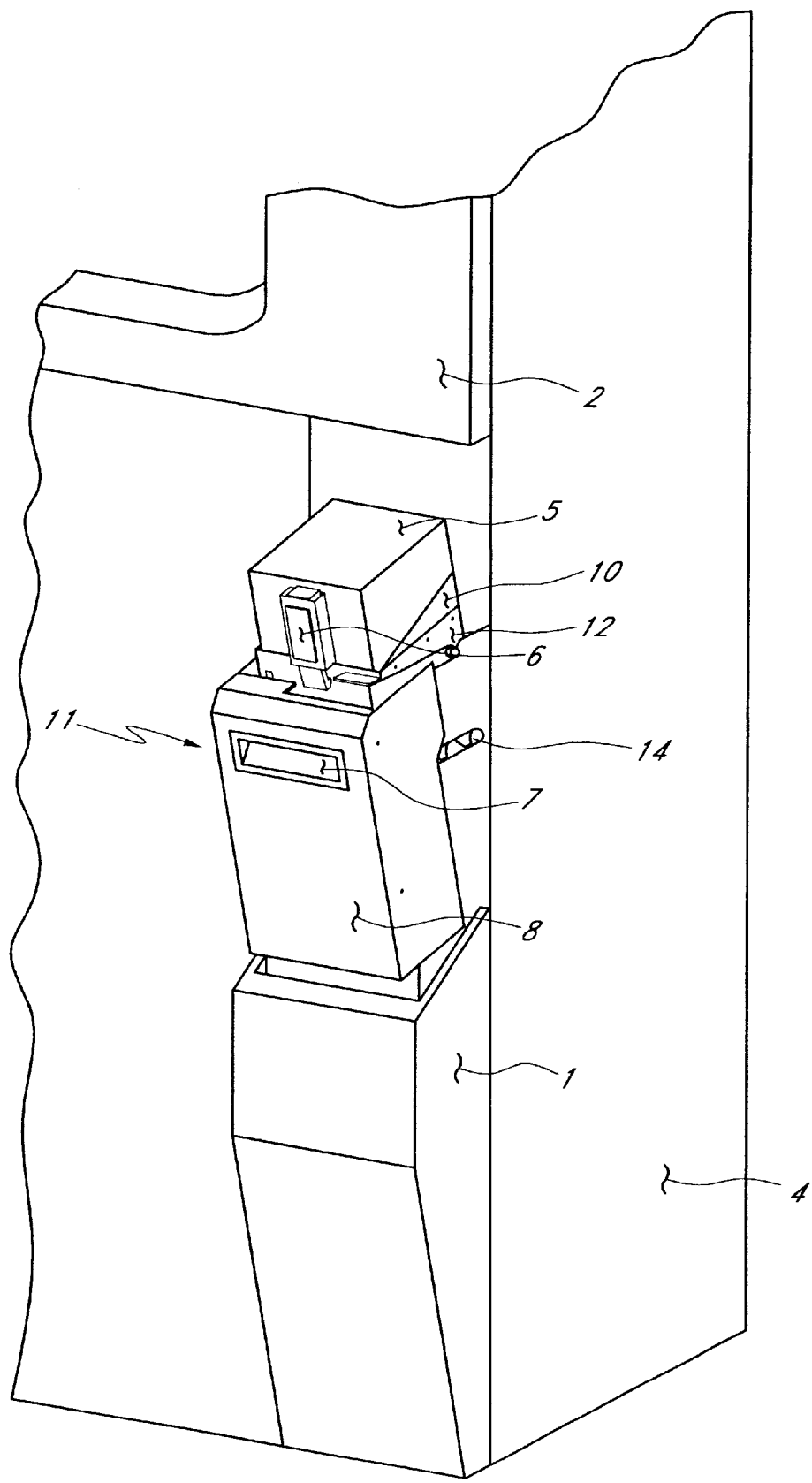
FIG. 2 is a perspective view of a container delivering system in the open position.
Figure 3:
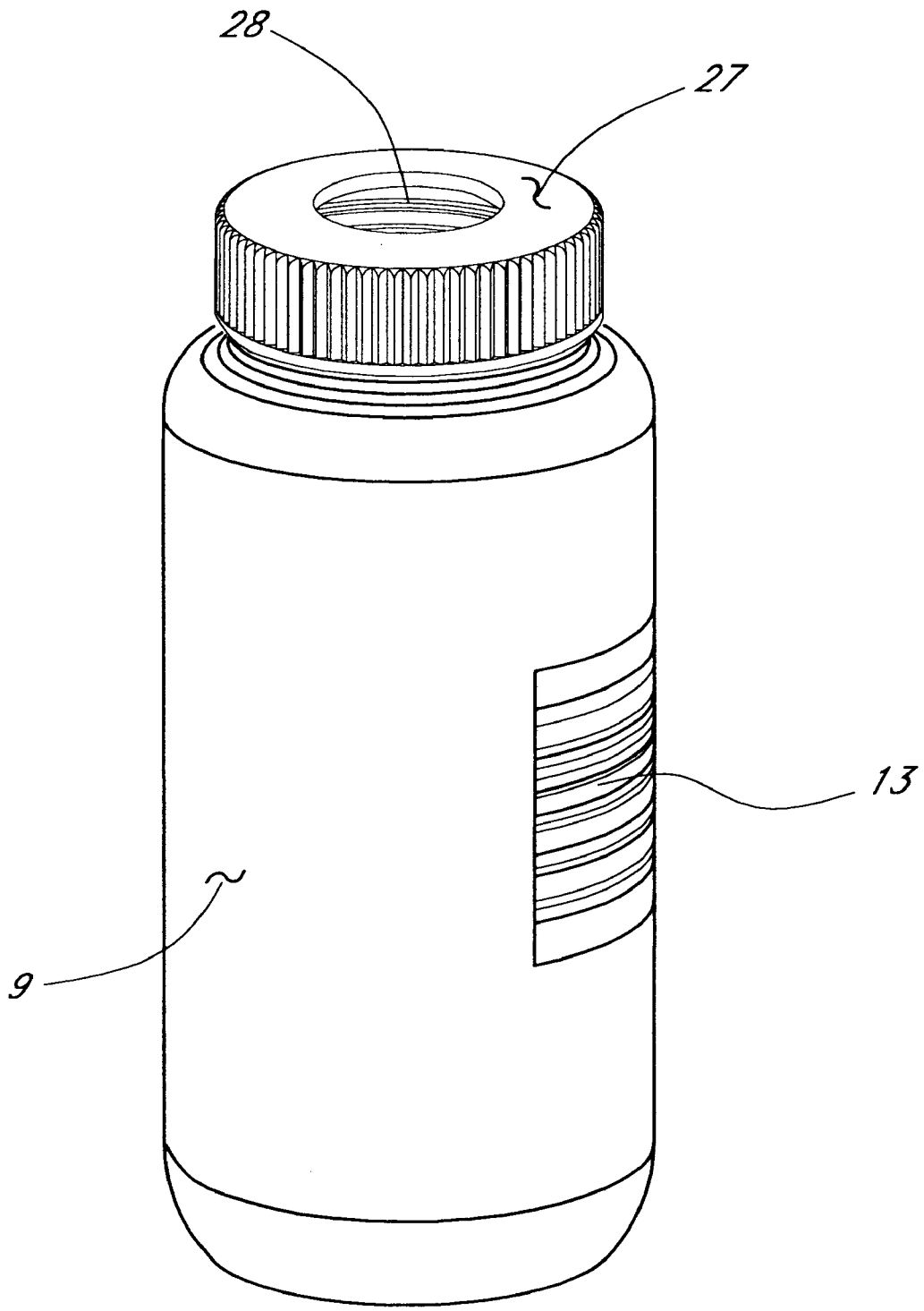
FIG. 3 is a perspective view of a container holding liquid sterilant.

Referring to the drawings, FIGS. 1 and 2 depict a container delivering system. FIG. 3 depicts a container which can be loaded into the system of FIGS. 1 and 2.

FIG. 1 generally depicts a container delivering system in a closed position. In the embodiment illustrated, the system includes both the container delivering system and a metering system enclosed in one structure. The metering system, discussed in further detail below, is encased behind the delivery panel 1. A vaporization chamber can be enclosed in the front panel 2, located above the container delivering system. Maintenance, repair, or other service can be accomplished via access through a service panel 3 or a side panel 4. The external components of the container delivering system comprise a lid 5, a latch 6, a pocket handle 7, and a fascia 8.

FIG. 2 illustrates this same embodiment in the open position. A container 9 (as shown in FIG. 3) containing a liquid, such as a liquid sterilant, liquid disinfectant, or any liquid germicide, can be loaded into the open container carrier 10 once an operator has pulled the fascia 8 out and away from the system structure by pulling on the pocket handle 7. A container carrier assembly 11 comprising the lid 5, the container carrier 10, the guard 12, the latch 6, the pocket handle 7, and the fascia 8, pivots at an angle when the system is opened so that the lid 5 can be opened and a container 9 can be placed inside for delivering.

However, in the preferred embodiment, the operator will not be able to open the delivering system if the liquid in the container 9 to be loaded into the system is determined to be unacceptable. The determination of whether the liquid in the container 9 is acceptable for use can be accomplished, for example, by scanning a bar code 13 affixed to the container 9. As shown in FIG. 3, the bar code 13 can contain digitized information detailing the relevant data of the liquid sterilant stored in a particular container. Every container 9 has a unique bar code 13 to prevent the misuse of a container. As an example, the operator could use a movable bar code reader, mounted on or near the container delivering system, to scan the bar code 13 on the container 9 to be loaded.

Figure 4:
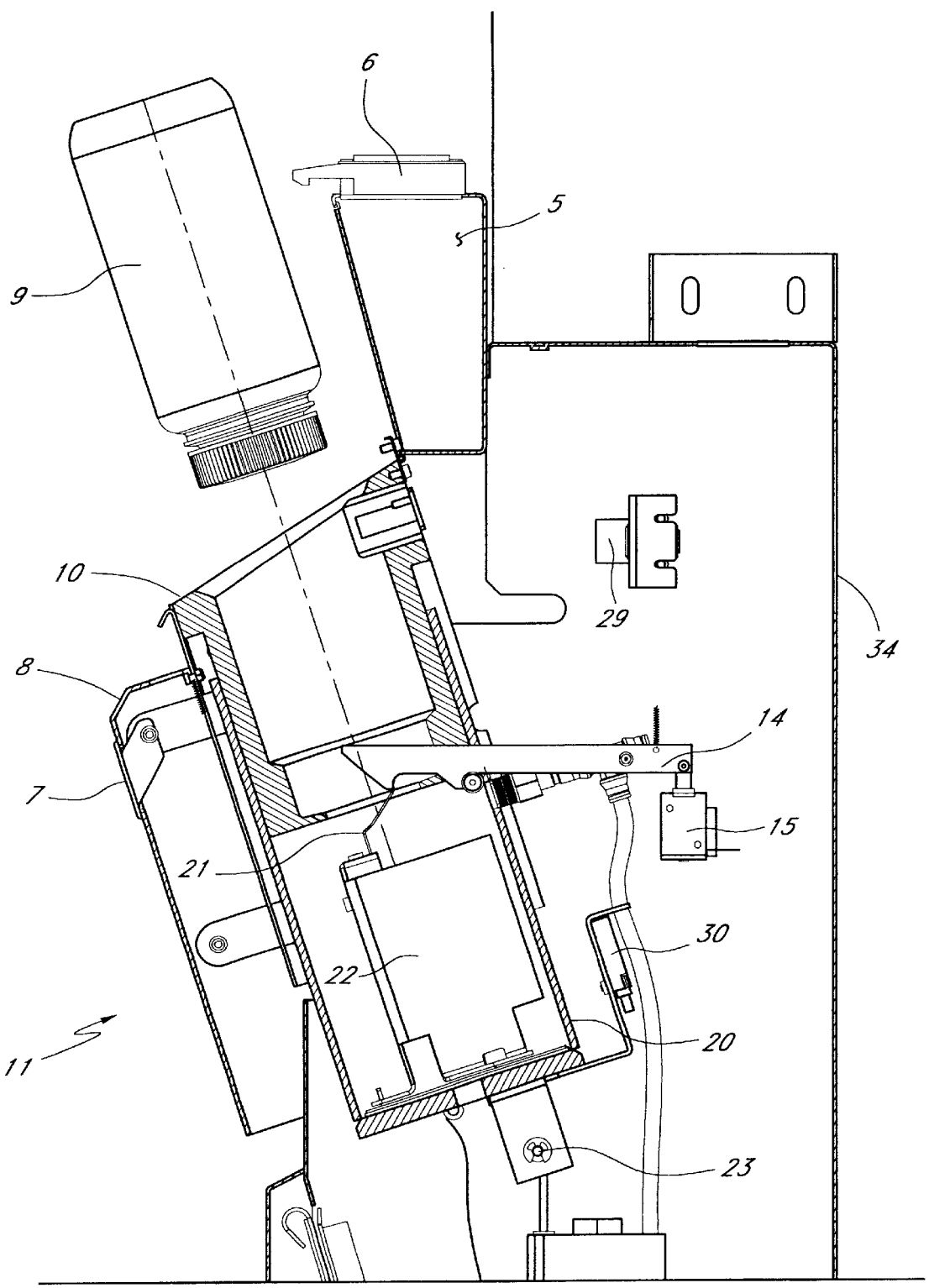
FIG. 4 is a detailed side view of a container delivering system in the open position ready for delivery of a container.

Referring now to FIG. 4, an interlock mechanism comprising a ratchet 14 and controlled by a solenoid 15 prevents opening of the delivering system if the liquid in the container 9 is determined to be unacceptable. If the container and the liquid contained therein are determined to be acceptable, then a solenoid 15 is activated to release the ratchet 14.

Figure 5:
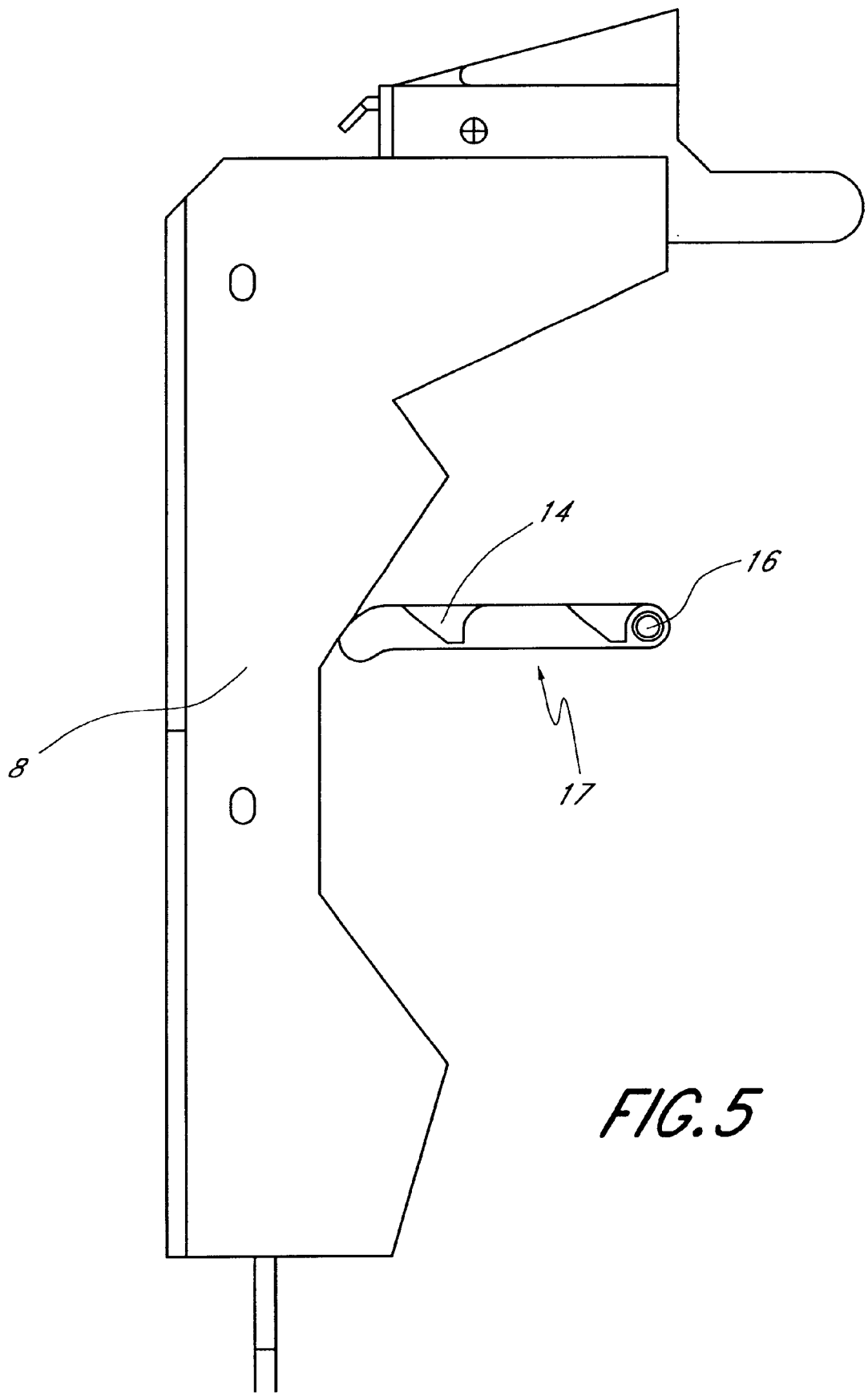
FIG. 5 is an exterior side view of a releasing mechanism for the container delivering system.
Figure 6:
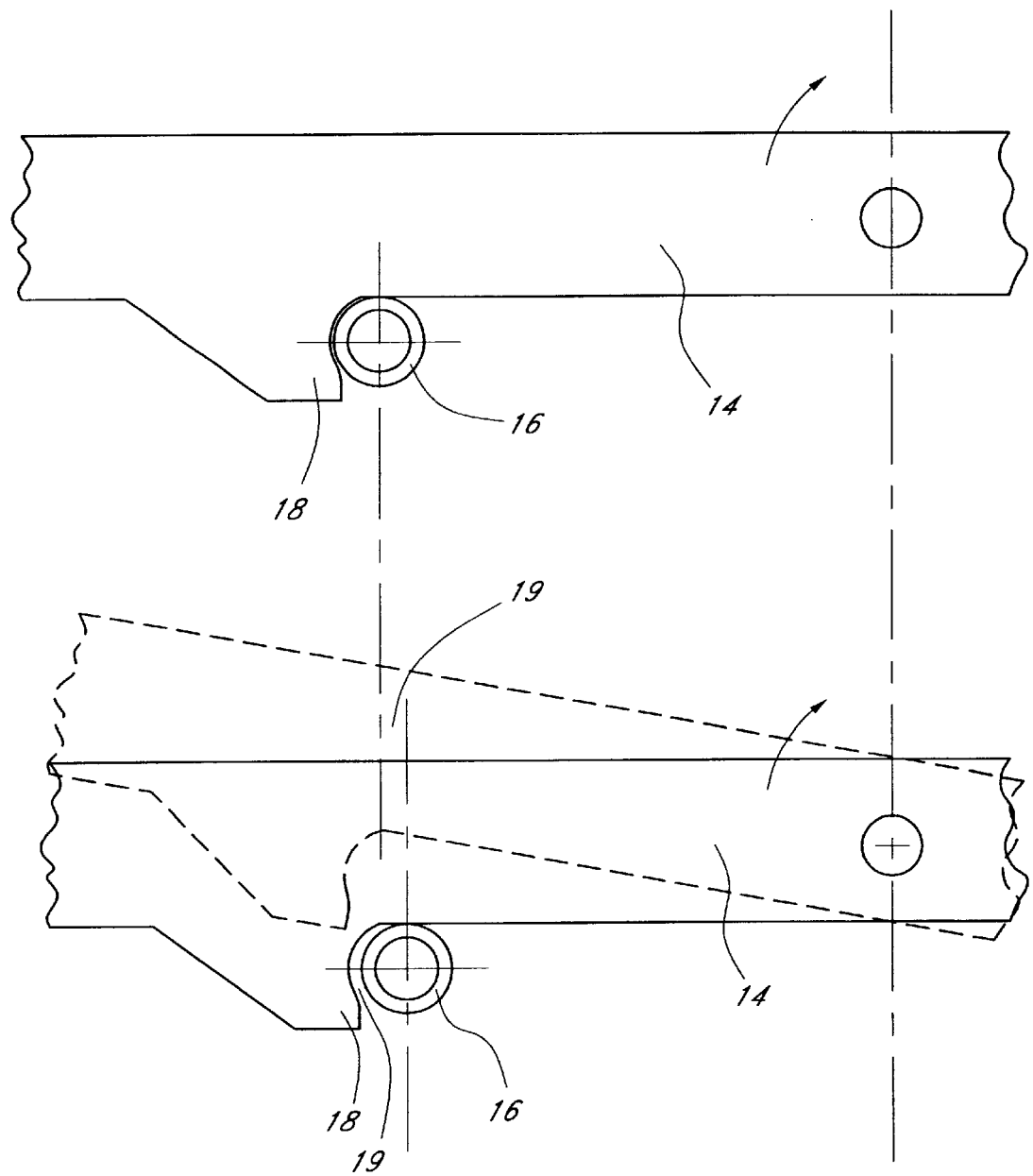
FIG. 6 is a detailed side view of the releasing mechanism in operation.

The side view of this interlock mechanism is depicted in FIGS. 2 and 5. A bearing 16 that is fixedly connected to the guard 12 and the container carrier 10 lies in a horizontal track 17. As shown in FIG. 6, the ratchet 14 is shaped with a tip 18 to prevent the lateral movement of the bearing 16 and thus the container carrier 10. Therefore, once the ratchet 14 is released to move by the solenoid 15, the bearing 16 remains prevented from movement by the tip 18 of the ratchet. To overcome this, the operator must push the container carrier 10 by the pocket handle 7 in, towards the structure. This movement created by the operator creates a gap 19 which allows the tip 18 of the ratchet 14 to clear the bearing 16. Once a gap 19 is created by the movement of the bearing 16 by the operator, the ratchet 14 pivots upward to release the bearing 16 to move laterally out within the track 17.

Figure 7:
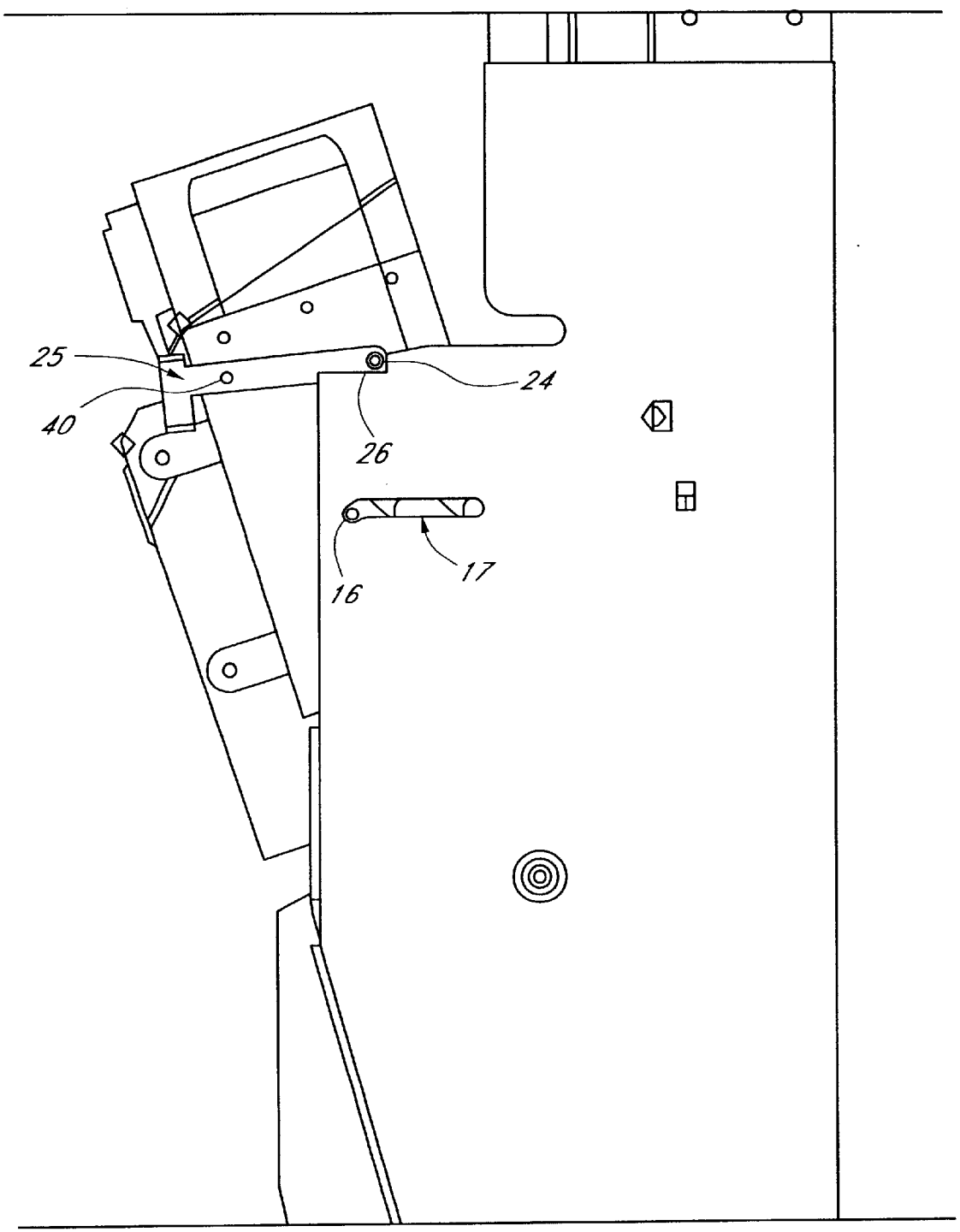
FIG. 7 is a detailed side view of a container delivering system in the open position with a container loaded.

Referring again to FIGS. 4 and 5, with the bearing 16 free to move laterally out within the track, the container carrier assembly 11 comprising the container carrier 10, the fascia 8, the accumulator 20, the blade 21 and a spike assembly 22, the pocket handle 7, the lid 5, and the latch 6 pivot about pivot 23. At the same time, the entire container carrier assembly 11 moves laterally as guided by the horizontal movement of the bearing 16 within the track 17. The end of the track 17 stops the lateral movement of the bearing 16 and hence blocks the further lateral and pivoting movement of the container carrier assembly 11. As shown in FIG. 7, as the bearing 16 comes to stop on the track 17, a pin 24 on a linkage 25 rotates about point 40 and rests on the ledge 26 to lock the container carrier assembly in place. Preferably, the linkage 25 keeps the container carrier 10 in the open position while delivering or undelivering the container 9 or while lifting the lid 5. In another embodiment, the container carrier 10 can also work without being locked in the open position by the linkage 25.

Referring back to FIG. 4, as the container carrier 10 is fully opened, the operator uses one hand to unlatch latch 6 and lift the lid 5 up, insert the container 9 with the cap 27 down into the container carrier 10, and close the lid 5 with a latch 6. This configuration is illustrated in FIG. 7 where the container 9 has been inserted into the container carrier 10. At this point, the container 9 is not punctured and the seal 28 on the cap 27 is ready to be punctured. In order to puncture the seal 28, the operator must close the container carrier 10 by pressing down the linkage 25 to unlock the container carrier 10 and then push the container carrier assembly 11 inward. This locking movement will force the container to move vertically down onto the spike assembly 22. A blade on the spike assembly will puncture the seal 28 of the container 9. The seal 28 of the container 9 will only be punctured after the ratchet 14 locks onto the bearing 16. The container carrier assembly 11 is locked in the closed position so that container 9 cannot be retrieved during or after the seal 28 is punctured by the spike assembly 22.

When the seal 28 is punctured by the blade 21, the contents of the container 9 are gravity-drained into the accumulator 20. In the preferred embodiment, the volume of the accumulator 20 is greater than the volume of the container 9. A significant advantage of this system is the reliance on gravity to manually load the container. Moreover, the system uses the closing mechanism of the door to puncture the seal on the container. These two features allow the design to be much more reliable than using pneumatics or solenoids to drive the container up and down to open the seal.

Once the container carrier 10 is closed, two sensors detect the container 9 and the liquid in the container 9. A container sensor 29 as shown in FIG. 4 detects the liquid flow out of the container 9 to ensure that the blade 21 breaks the seal 28. The level sensor 30 detects the liquid flowing into the accumulator 20 and detects the liquid when it is at a low level. If the accumulator is at a low-level mark, the level sensor 30 indicates to an operator by display that the system needs a new container loaded.

Figure 8:
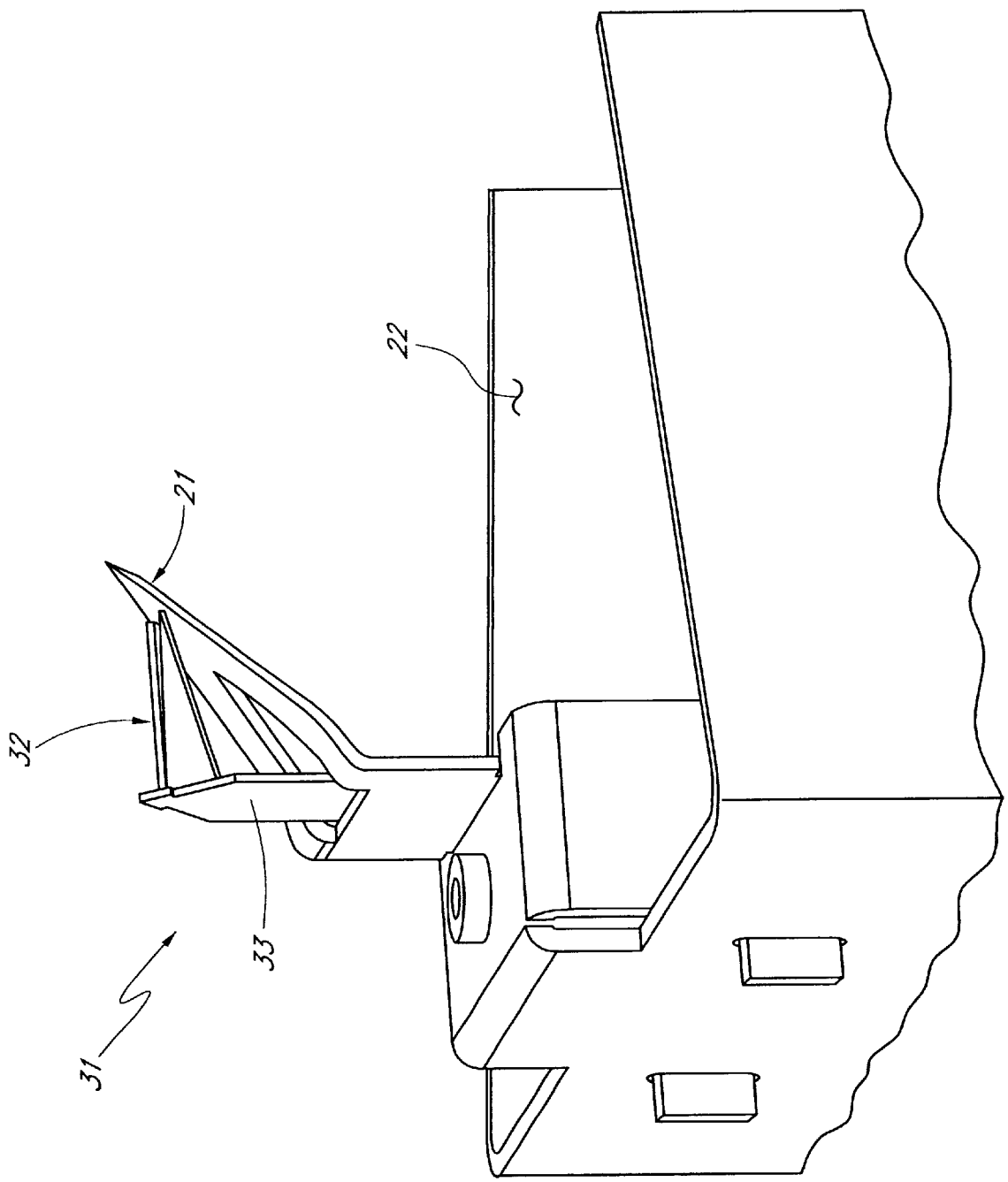
FIG. 8 is a detailed perspective view of a spike assembly.

In the preferred embodiment, the spike assembly 22 comprises an opening mechanism as illustrated in FIG. 8. The opening mechanism 31 is fixedly attached on top of the spike assembly 22. The opening mechanism 31 comprises two members positioned vertically with a separating mechanism 32 connected between the two members. One member is a blade 21 which serves as a first puncturing device and may be positioned at an angle to the vertical axis of the spike assembly. The second member is a second puncturing device 33 for the opening mechanism. When the container is lowered down onto the spike assembly as the container carrier assembly 11 is closed, the seal 28 of the container 9 is punctured by both the blade 21 and the second puncturing device 33 of the spike assembly. The blade 21 creates a first opening in the seal 28 and the second puncturing device 33 creates a second opening. As the container 9 is forced to move further downward, the separating mechanism 32 slices a slit between the first opening in the seal 28 and the second opening. As the container 9 is forced to move further downward into position, the separating mechanism 32 widens the slit. This process allows the opening mechanism of the spike assembly 22 to create a sufficient opening in the seal 28 of the container 9 such that any liquid contained therein can more easily gravity drain into the accumulator 20.

The container delivering system is designed to reliably determine if the liquid sterilant in the container 9 and the accumulator 20 is acceptable to use and to inform the user of the determination. If the liquid sterilant in the accumulator 20 is determined to be unacceptable, the user can purge the liquid sterilant to the drain container 36 as shown in FIG. 9 and described below.

Once a container 9 is loaded into the container delivering system and the liquid sterilant is directed into an accumulator, a metering system then dispenses the liquid sterilant to the vaporizer when needed. FIG. 9 illustrates a schematic view of a metering system and FIG. 10 depicts a side view of the metering system. The metering system is designed so that it will reliably transfer predetermined quantities of liquid sterilant such as hydrogen peroxide to a vaporizer for sterilization of medical devices and apparatus.

In one embodiment, the metering system will be controlled by software to deliver an amount of liquid sterilant, such as liquid hydrogen peroxide, when an injection is required. The software will turn on or off four valves together with vacuum available inside the chamber to drive pre-determined quantities of liquid hydrogen peroxide from the metering tube to the vaporizer. These valves are depicted in FIG. 9 as valve #1 71, valve #2 72, valve #3 73, and valve #4 74.

Figure 9:
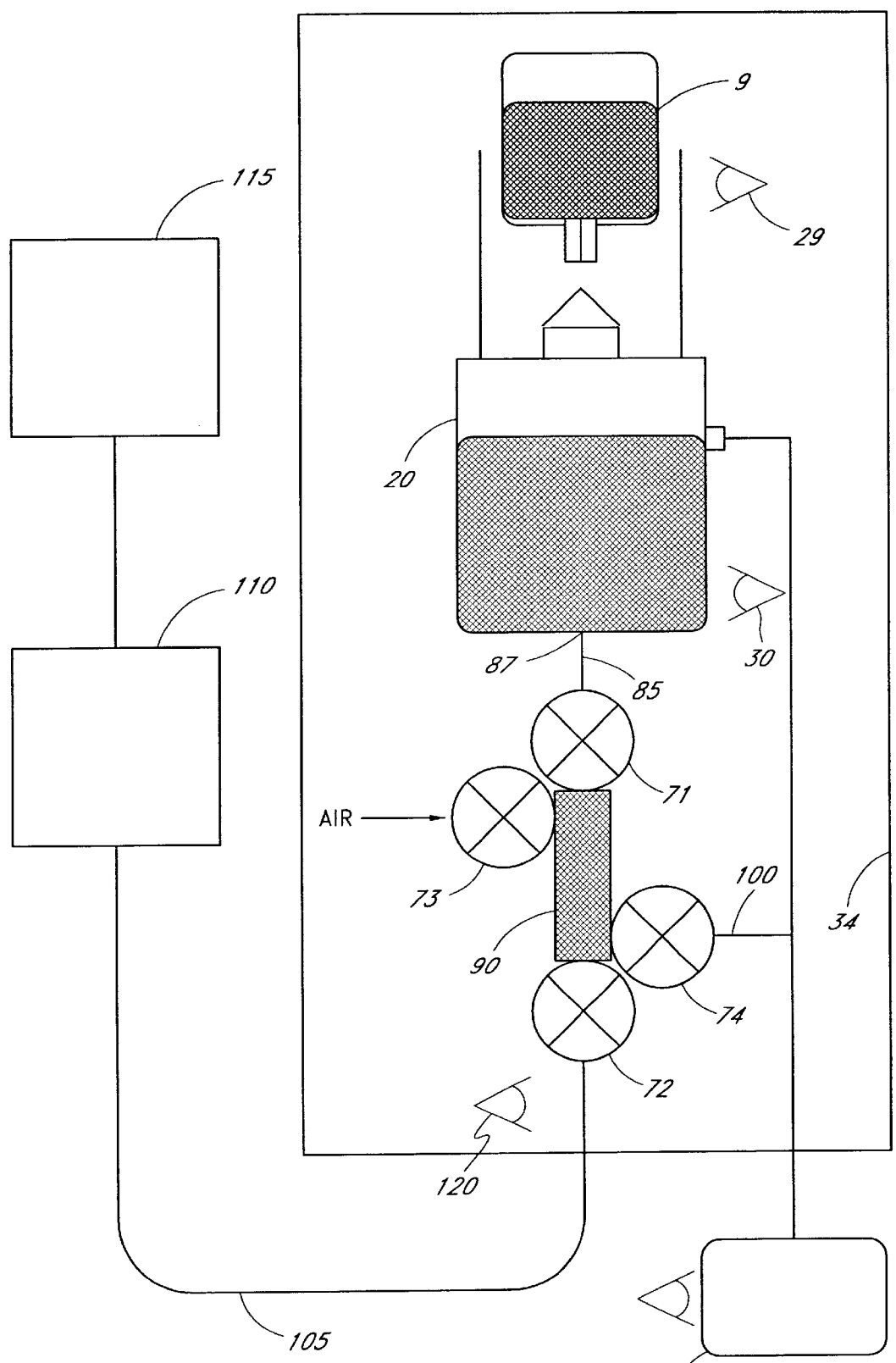
FIG. 9 is a schematic view of a metering system.
Figure 10:
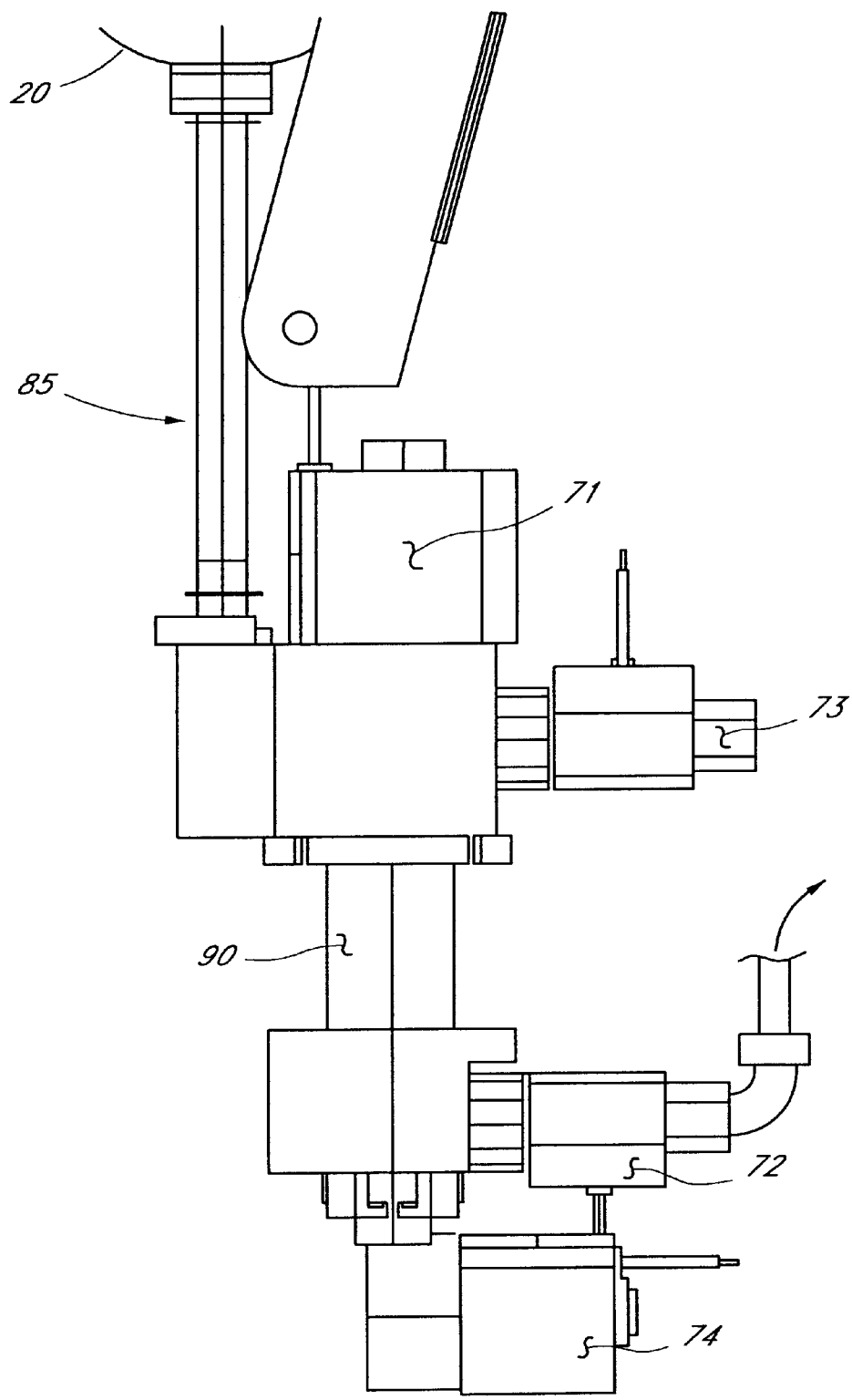
FIG. 10 is a detailed side view of a metering system.

Referring to FIGS. 9 and 10, one embodiment of the metering system includes a metering tube 90 into which liquid sterilant from an accumulator 20 can be dispensed. As described above, the level sensor 30 of the accumulator 20 can provide indication of the level of liquid sterilant in the accumulator 20. A dispensing tube 85 of small diameter (for example ¼ inches) leads from the bottom of the accumulator 20 to a valve #1 71. In the preferred embodiment, a screen 87 is located between the accumulator 20 and the dispensing tube 85 (or in the accumulator 20) prevents any solid particulates from being passed to the metering tube 90. Valve #1 71 is connected to the metering tube 90. A second valve, valve #3 73, which is connected to an air source, is also connected to the metering tube 90. The volume of the metering tube 90 is fixed. The metering tube is connected to two more valves, valve #2 72 and valve #4 74. A purging tube 100 extends from valve #4 74 to allow for purging of unacceptable liquid sterilant. An injection tube 105 extends from valve #2 72 into a vaporizer 110 to allow for injection of the liquid sterilant into the vaporizer 110. The vaporizer is fluidly connected to a sterilization chamber 115 which can be placed under a vacuum.

As shown in FIG. 9, the container delivering system provides a secondary container 34 to house the container 9, an accumulator 20, and the metering system. If the container delivering system experiences a leakage or an overflow, the secondary container 34 will keep the spilled liquid inside the closed system.

FIG. 11 depicts a table listing the various states of the metering method employed by one embodiment of the metering system. In state 1, the system is idle, and all four valves (that is, valve #1 71, valve #2 72, valve #3 73, and valve #4 74) are closed. At state 2, the metering tube 90 is evacuated when valve #2 72 opens. The metering tube 90 is filled with liquid sterilant from the accumulator 20 by closing valve #2 72 and opening valve #1 71 in state 3. Next, in state 4, the liquid sterilant is injected into the vaporizer 110 by first closing valve #1 71, opening valve #2 72, and then, after a short delay, opening valve #3 73. Following the injection of the metered liquid sterilant into the vaporizer 110, a flow sensor 120 senses air in the injection tube following valve #2 72 and will prompt the closing of valve #3 73 in state 5. At this point, the metering process is complete. The valve #2 72 is then closed and ready for the next injection. State 6 represents the configuration when liquid sterilant in the accumulator 20 is determined to be unacceptable for use and can be purged from the system by opening valve #1 71 and valve #4 74. The unacceptable liquid sterilant is gravity drained from the accumulator 20 through the purging tube 100 into a drain container 36.

In the embodiment described above, the size and diameter of the injection tube 105 is smaller than the size and diameter of valve #1 71 and dispensing tube 85. For example, valve #1 71 and dispensing tube 85 can have ¼ inch diameter to allow for the liquid sterilant to fill the metering tube 90 more quickly. In this same example, valve #2 72 and the injection tube 105 could have ¹/₁₆ inch diameter. The smaller diameter will allow for slower flow. Slower flow into the vaporizer maximizes the efficiency of vaporization by allowing the vaporizer to remain hot during the vaporization state. Slower flow also improves the accurate sensing of the air/liquid interface in the injection tube 105.

Throughout these states, a vacuum can be placed on the sterilization chamber 115. In states 2 and 3, a vacuum can be placed on the sterilization chamber while the metering and injection tubes are evacuated and the metering tube is filled. During injection of the liquid sterilant in states 4 and 5, the vacuum on the sterilization chamber 115 can be turned off. During purge in state 6, the vacuum on the sterilization chamber 115 can be either on or off. A vacuum can always be off in state 1 when the metering system is idle. By using the vacuum available in the sterilization chamber to drive liquid sterilant into the vaporizer, there is no need to use any pumps to deliver liquid into the vaporizer.

While the above detailed description has shown, described and pointed out fundamental novel features of the invention as applied to various embodiments, it will be understood that various omissions and substitutions and changes in the form and details of the device illustrated may be made by those skilled in the art, without departing from the spirit of the invention. For example, while the present invention has been described with respect to use in a sterilization system, it should, of course, be understood that a system and method of delivering and metering can be applied to other systems in which it is desirable to improve the efficiency and effectiveness of dispensing fixed volumes of liquid into a container.

What is claimed is:

1. A delivery system of delivering a liquid from a container into an accumulator, the system comprising:
   the container for delivering the liquid into the accumulator, said container comprising a puncturable seal;
   the accumulator for receiving the liquid from the container;
   a first sensor to determine a first pre-defined specification of the liquid in the accumulator;
   a first delivery mechanism for loading the container into a container carrier;
   a second delivery mechanism for delivering the liquid in the container into the accumulator;
   a release mechanism for releasing the container carrier of the delivery system; and
   a locking mechanism for securing the container in the delivery system.

2. The delivery system of claim 1, wherein the liquid is a germicide.

3. The delivery system of claim 1, wherein the container holds a fixed volume of liquid.

4. A The delivery system of claim 1, wherein the capacity of the accumulator is greater than the capacity of the container.

5. The delivery system of claim 1, wherein the container comprises a removable sealing mechanism to retain the liquid in the container.

6. The delivery system of claim 1 further comprising an opening mechanism to puncture the seal of the container.

7. The delivery system of claim 1, wherein the first sensor detects the level of the liquid in the accumulator.

8. The delivery system of claim 1 further comprising a second sensor to determine a second pre-defined specification of the container.

9. The delivery system of claim 8, wherein the second sensor is a bar code scanner.

10. The delivery system of claim 8, wherein the second pre-defined specification is lot code information.

11. The delivery system of claim 8 further comprising a third sensor to detect the flow of liquid from the container into the accumulator.

12. A delivery system of delivering a liquid from a container into an accumulator, the system comprising:
    the container for delivering the liquid into the accumulator;
    the accumulator for receiving the liquid from the container;
    a first sensor to determine a first pre-defined specification of the accumulator;
    a second sensor to determine a second pre-defined specification of the container;
    a first delivery mechanism for loading the container into a container carrier;
    a second delivery mechanism for delivering the liquid in the container into the accumulator;
    a release mechanism for releasing the container carrier of the delivery system; and
    a locking mechanism for securing the container in the delivery system.

13. The delivery system of claim 12, wherein the second sensor is a bar code scanner.

14. The delivery system of claim 12, wherein the second predefined specification is lot code information.

15. The delivery system of claim 12, further comprising a third sensor to detect the flow of liquid from the container into the accumulator.

16. A method of delivering a liquid from a container into an accumulator via a container delivery system, the method comprising:
    determining whether the liquid in the accumulator satisfies a first pre-defined specification;
    generating a signal prompting the loading of the container into the container delivery system;
    releasing the container delivery system to accept the loading of the container into the container delivery system;
    loading the container into the container delivery system;
    closing the container delivery system;
    locking the container delivery system to secure the container in the container delivery system; and
    delivering the liquid from the container into the accumulator by puncturing a seal on the container.

17. The method of claim 16, wherein the liquid is a germicide.

18. The method of claim 16, further comprising sensing the flow of liquid from the container to the accumulator.

19. The method of claim 16, wherein the puncturing a seal on the container occurs at the same time as the closing of the container delivery system.

20. The method of claim 16, wherein the container delivery system comprises a container carrier assembly with a locking mechanism.

21. The method of claim 16, wherein the releasing the container delivery system to accept the loading of the container into the container delivery system comprises:

pushing the container carrier assembly in towards the container delivery system in order to release the locking mechanism; and pulling the container carrier assembly out away from the container delivery system after the locking mechanism is released.

22. The method of claim 16, wherein the determining whether the liquid in the accumulator satisfies a first pre-defined specification comprises sensing the level of the liquid in an accumulator.

23. The method of claim 16, further comprising determining whether the liquid in the container satisfies a second pre-defined specification.

24. The method of claim 23, wherein the determining whether the liquid in the container satisfies a second pre-defined specification comprises sensing an identifier unique to the container.

25. The method of claim 23, wherein the identifier unique to the container is a bar code.

26. The method of claim 23, wherein the second pre-defined specification is lot code information.

27. A method of delivering a liquid from a container into an accumulator via a container delivery system, the method comprising:

determining whether the liquid in the accumulator satisfies a first pre-defined specification;

generating a signal prompting the loading of the container into the container delivery system;

releasing the container delivery system to accept the loading of the container into the container delivery system by pushing the container carrier assembly in towards the container delivery system in order to release the locking mechanism; and pulling the container carrier assembly out away from the container delivery system after the locking mechanism is released;

loading the container into the container delivery system;

closing the container delivery system;

locking the container delivery system to secure the container in the container delivery system; and delivering the liquid from the container into the accumulator.

28. A method of delivering a liquid from a container into an accumulator via a container delivery system, the method comprising:

determining whether the liquid in the accumulator satisfies a first pre-defined specification;

generating a signal prompting the loading of the container into the container delivery system;

releasing the container delivery system to accept the loading of the container into the container delivery system;

loading the container into the container delivery system;

determining whether the liquid in the container satisfies a second pre-defined specification;

closing the container delivery system;

locking the container delivery system to secure the container in the container delivery system; and delivering the liquid from the container into the accumulator.

29. A method of delivering a liquid from a container into an accumulator via a container delivery system, the method comprising:

determining whether the liquid in the accumulator satisfies a first pre-defined specification;

generating a signal prompting the loading of the container into the container delivery system;

releasing the container delivery system to accept the loading of the container into the container delivery system;

loading the container into the container delivery system;

closing the container delivery system;

locking the container delivery system to secure the container in the container delivery system;

delivering the liquid from the container into the accumulator; and sensing the flow of liquid from the container to the accumulator.

* * * * *